United States Patent
Wei et al.

(10) Patent No.: US 11,925,728 B2
(45) Date of Patent: Mar. 12, 2024

(54) DEGRADABLE VASCULAR STENT CAPABLE OF AVOIDING LATE RESTENOSIS

(71) Applicant: Shanghai Weite Biotecnnology Co., Ltd, Shanghai (CN)

(72) Inventors: Zheng Wei, Shanghai (CN); Bin Huang, Shanghai (CN); Jian Xie, Shanghai (CN); Yunhong Mu, Shanghai (CN)

(73) Assignee: Shandong Huaan Biotechnology Co., Ltd., Jinan (CN)

( * ) Notice: Subject to any disclaimer, the term of this patent is extended or adjusted under 35 U.S.C. 154(b) by 916 days.

(21) Appl. No.: 16/960,258

(22) PCT Filed: Jan. 9, 2018

(86) PCT No.: PCT/CN2018/071913
§ 371 (c)(1),
(2) Date: Jul. 6, 2020

(87) PCT Pub. No.: WO2019/136593
PCT Pub. Date: Jul. 18, 2019

(65) Prior Publication Data
US 2021/0069384 A1   Mar. 11, 2021

(51) Int. Cl.
*A61F 2/06* (2013.01)
*A61F 2/90* (2013.01)
(Continued)

(52) U.S. Cl.
CPC ............... *A61L 27/54* (2013.01); *A61F 2/06* (2013.01); *A61F 2/90* (2013.01); *A61L 27/18* (2013.01);
(Continued)

(58) Field of Classification Search
CPC ...... A61F 2250/0068; A61F 2250/0067; A61F 2/90; A61F 2002/91533;
(Continued)

(56) References Cited

U.S. PATENT DOCUMENTS

| 9,750,852 B2 | 9/2017 | Mortisen et al. |
| 2011/0009949 A1* | 1/2011 | Stankus ................. A61L 31/14 623/1.15 |
| 2011/0118827 A1 | 5/2011 | Wu |

FOREIGN PATENT DOCUMENTS

| CN | 1367023 | 9/2002 |
| CN | 101264345 | 9/2008 |

(Continued)

*Primary Examiner* — Matthew J Lawson
*Assistant Examiner* — Rebecca Lynee Zimmerman
(74) *Attorney, Agent, or Firm* — Boyle Fredrickson, S.C.

(57) ABSTRACT

The present invention relates to a degradable vascular stent capable of avoiding late restenosis, comprising a base region formed by a polylactic acid based polymer; at least one storage region in which an active agent is stored; and an outer layer of a drug sustained release coating covered on the base region and/or the storage region. Before the mass of the polylactic acid based polymer is decreased by 10-20%, the active agent is retained in structural units of the polylactic acid based polymer. After the mass of the polylactic acid based polymer is decreased by 10-20%, the active agent is released from the storage region. The base region provides a supporting capacity for ensuring patency of blood vessels; the drug sustained release coating is used for drug release in an early stage; and the active agent only works in late degradation of the stent to avoid late restenosis.

10 Claims, 6 Drawing Sheets

(51) Int. Cl.
*A61L 27/18* (2006.01)
*A61L 27/26* (2006.01)
*A61L 27/54* (2006.01)
*A61L 27/58* (2006.01)

(52) U.S. Cl.
CPC ............... *A61L 27/26* (2013.01); *A61L 27/58* (2013.01); *A61F 2210/0004* (2013.01); *A61F 2250/0068* (2013.01); *A61L 2300/41* (2013.01); *A61L 2300/412* (2013.01); *A61L 2300/42* (2013.01)

(58) Field of Classification Search
CPC ............ A61F 2002/91566; A61F 2/915; A61F 2/82–2002/9665; A61L 27/54; A61L 27/18; A61L 27/26; A61L 27/58; A61L 2300/41; A61L 2300/412; A61L 2300/42; A61L 31/148; A61L 31/06; A61L 31/16
See application file for complete search history.

(56) References Cited

FOREIGN PATENT DOCUMENTS

| | | |
|---|---|---|
| CN | 101327343 | 12/2008 |
| CN | 104524637 | 4/2015 |
| CN | 106310395 | 1/2017 |
| EP | 1611920 | 1/2006 |

* cited by examiner

DEGRADABLE VASCULAR STENT CAPABLE OF AVOIDING LATE RESTENOSIS

CROSS REFERENCE TO RELATED APPLICATIONS

This application is a Section 371 U.S. National Phase Entry of International Patent Application No. PCT/CN2018/071913, filed on Jan. 9, 2018, the contents of which are all hereby incorporated by reference.

FIELD OF THE INVENTION

The present invention relates to a degradable vascular stent, and more particularly to a degradable vascular stent capable of avoiding late restenosis.

BACKGROUND OF THE INVENTION

Due to their excellent efficacy and good safety, degradable stents have initially had the potential to replace drug eluting stents (DESs) widely used in clinical practice. Degradable stents are even hailed as the fourth revolutionary development in the history of interventional cardiology, becoming one of the main performers of the present popular vascular repair therapy.

The present popular degradable stents mainly focus on polylactic acid and its copolymerized or blended materials. Such material can be collectively referred to as polylactic acid based polymer. In 2011, the world's first fully degradable coronary stent was developed using polylactic acid in the United States and was approved for sale in Europe, which marked the start of the commercialization of degradable polymer stents.

However, despite the good biocompatibility of polylactic acid based polymer, the large amount of lactic acid released after degradation and the reconstruction of blood vessel tissue during degradation will stimulate local blood vessels to cause inflammation, which has been proved to be related to late restenosis in stent (In Stent Restenosis, ISR) and stent thrombosis.

SUMMARY OF THE INVENTION

By wat of summary, in order to solve the above-mentioned problem of inflammation caused by the degradation of polylactic acid based polymer in the prior art, the present invention aims to provide a degradable vascular stent capable of avoiding late restenosis.

The present invention provides a degradable vascular stent capable of avoiding late restenosis, comprising: a base region formed by a polylactic acid based polymer; at least one storage region in which an active agent is stored; and an outer layer of a drug sustained release coating covered on the base region and/or the storage region. Before the mass of the polylactic acid based polymer of the base region is decreased by 10-20%, the active agent in the storage region is retained in structural units of the polylactic acid based polymer. After the mass of the polylactic acid based polymer of the base region is decreased by 10-20%, the active agent in the storage region is released from the storage region.

The polylactic acid based polymer includes, but is not limited to, a bulk degradation polymer degradable to release acidic monomers or components, such as polylactic acid (PLA), polyglycolic acid (PGA), polyhydroxybutyrate (PHB), poly(lactic-co-glycolic acid) (PLGA), poly(polyethylene glycol (polypropylene glycol)-co-lactic acid) (PELA), polycaprolactone (PCL), polyalkylcyanoacrylate (PACA), poly(L-lactide)-block-poly(ethylene glycol) (PLA-PEG), poly(ε-caprolactone-block-L-lactide), and mixtures of the above-mentioned polymers in any ratio.

The storage region is formed of an alkaline degradable polymer or a mixture of a polylactic acid based polymer and an alkaline degradable polymer. After the mass of the polymer of the base region is decreased by 10-20%, the alkaline degradable polymer is hydrolyzed to release alkaline monomers.

The alkaline degradable polymer is chitosan or sodium alginate.

The storage region is formed of a mixture of an alkaline salt dispersed in a polylactic acid based polymer. After the mass of the polymer of the base region is decreased by 10-20%, the alkaline salt is hydrolyzed to release alkaline monomers.

The alkaline salt is selected from the group consisting of sodium carbonate, sodium bicarbonate, potassium carbonate, calcium carbonate, sodium sulfite, sodium acetate, sodium sulfide, ferrous sulfide, sodium silicate, sodium phosphate, sodium metaaluminate, sodium hypochlorite, calcium hypochlorite, ammonium bicarbonate, copper hydroxoliodate, antimony dioxide sulphate, malachite, hydroxyapatite, cupric subcarbonate, or basic magnesium chloride.

The storage region is formed of a drug or a uniform mixture of a polylactic acid based polymer and a drug.

The drug is selected from the group consisting of an anti-thrombotic drug, an analgesic and anti-inflammatory drug, an anti-vascular smooth muscle cell proliferation drug, an anti-vascular smooth muscle cell migration drug, an endothelialization promoting drug, or a hormonal anti-inflammatory drug.

The degradable vascular stent also comprises a coating isolation region covered by the outer layer.

The storage region is a coating storage region on the base region, an embedded storage region in the base region, an integrated storage region formed integrally with the base region, or a layered storage region inside the base region.

According to the degradable vascular stent capable of avoiding late restenosis of the present invention, the base region serves as a main body to mainly provide a supporting capacity for ensuring the patency of blood vessels; the drug sustained release coating covered on the base region is used for drug release in an early stage after implantation; and the active agent stored in the storage region only works in late degradation of the stent to avoid late restenosis. The active agent released at a late stage is for anti-inflammatory reaction. For example, the alkaline degradable polymer is used to neutralize lactic acid monomers, and the drug is used to inhibit intimal inflammation or hyperplasia. Thus the rejection reaction between the stent and the vascular endothelium tissue after implantation is fundamentally solved. In addition, the overall degradation products of the degradable vascular stent capable of avoiding late restenosis of the present invention are safe and reliable without any damage to the human body.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWING

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

Figure 1:
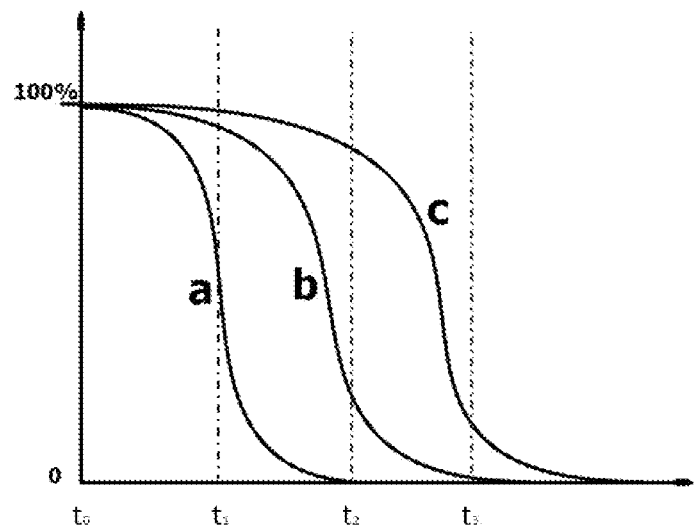
FIG. 1 is a typical degradation curve of the polylactic acid based polymer.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose.

DESCRIPTION OF THE PREFERRED EMBODIMENTS

The preferred embodiments of the present invention will be described in detail in conjunction with the drawings.

The degradation of the polylactic acid based polymer for forming the degradable vascular stent is due to bulk degradation. The decomposition, dissolution or molecular weight decrease occurs on the surface and inside of the material at the same time, resulting in the strength decrease and eventual disintegration of the material.

After the polylactic acid based polymer is implanted into the human body, the polymer absorbs water at first. The aqueous medium penetrates into the polymer matrix, causing polymer molecular chains to relax and ester bonds to pre-hydrolyze, and thus the molecular weight of the polymer decreases and the polymer is gradually degraded into oligomers. Such hydrolysis is catalyzed by terminal carboxyl groups of polylactic acid (introduced by polymerization and produced by degradation). As the degradation proceeds, the terminal carboxyl group amount increases and the degradation rate accelerates, resulting in a self-catalysis. The internal degradation of polylactic acid based polymer is faster than the surface degradation, since the degradation product of terminal carboxyl group stays inside the polymer to produce a self-acceleration.

As the degradation continues, there will be more and more carboxyl groups inside the polymer to accelerate the degradation of the internal polymer, further increasing the difference between inside and outside. When the internal polymer is completely converted into soluble oligomers and dissolved in the aqueous medium, a hollow structure is formed with a surface composed of polymers that are not completely degraded. Only further degradation can cause the oligomers to hydrolyze into small molecules and finally be dissolved in the aqueous medium.

The entire dissolution process turns the water-insoluble solids into water-soluble substances. Macroscopically, as the overall structure is destroyed and the volume is reduced, the polymer gradually becomes fragments and is finally completely dissolved and absorbed or excreted by the body. Microscopically, as macromolecular chains are chemically broken, such as the molecular weight is reduced or molecular chain or side chain breaks, etc., the polymer is decomposed into water-soluble small molecules that enter body fluids and are swallowed by cells to be transformed and metabolized.

During the gradual degradation of the material, the internal degradation rate is faster than the surface degradation rate. Therefore, cells enter the interior of the material through the crack or gap, and grow in the micropores formed by degradation to gradually replace the stent. During the replacement, the remaining stent material is still rigid relative to the tissue cells. As the blood vessels expand and contract and peristaltic, the stent and cells rub against each other, further causing inflammation of the cells.

FIG. 1 shows a degradation curve of the polylactic acid based polymer. Curve a) refers to the degradation curve of the molecular weight of structural units of the polylactic acid based polymer. Curve b) is the loss curve of the polymer strength of the polylactic acid based polymer. Curve c) is the degradation curve of the polymer mass of the polylactic acid based polymer. From $t_0$ to $t_1$, the molecular weight of structural units for curve a) is decreased steadily; the polymer strength for curve b) is decreased slightly; and the polymer mass c) remains unchanged. From $t_1$ to $t_2$, the molecular weight of structural units for curve a) is decreased rapidly; the polymer strength for curve b) begins to decrease significantly; and the polymer mass for curve c) is decreased slightly. From $t_2$ to $t_3$, the molecular weight of structural units for curve a) is decreased continually, with nearly all becoming small molecule; the polymer strength for curve b) is decreased continually, with the strength gradually disappearing; and the polymer mass for curve c) is decreased significantly, with eventual disintegration completed. The $t_1$ is selected as the time point of the polymer strength for curve b) decreased by 10-20%. The $t_2$ is selected as the time point of the polymer mass for curve c) decreased by 10-20%. The $t_3$ is selected as the time point of the polymer mass for curve c) decreased by 80-90%.

During the period $t_0$-$t_2$, the polylactic acid based polymer gradually decomposes from the high polymer to the oligomer. During the period $t_2$-$t_3$, the polylactic acid based polymer is hydrolyzed from the oligomer to lactic acid monomers, which are finally dissolved in the aqueous medium. Of course, there are also hydrolyzed lactic acid monomers during the period $t_0$-$t_2$, but they can be normally consumed through the metabolism of the human body due to the relatively small amount. In contrast, during the period $t_2$-$t_3$, large amount of lactic acid monomers are released and the human body has no time to decompose and devour so many lactic acid monomers, causing local acidity increase and inflammation.

Obviously, polylactic acid based stents may have different degradation cycles due to different materials, thus inflammation may be appeared at different time. For example, the period $t_2$-$t_3$ may cover 1-2 years or 1.5-2.5 years or 2-3 years after implantation of the stent.

Figure 2:
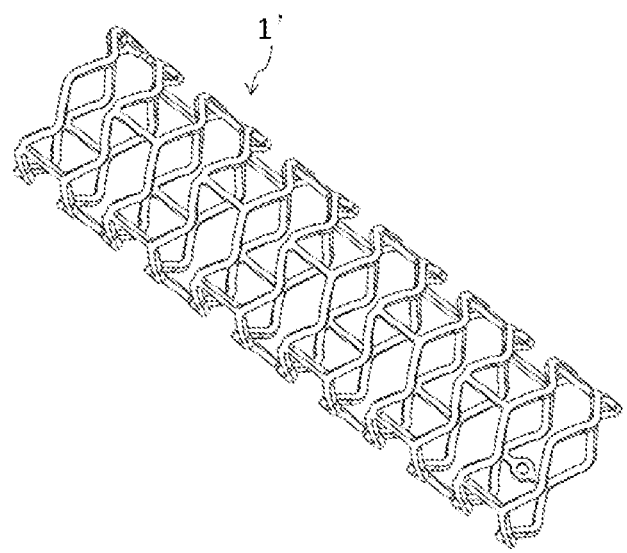
FIG. 2 is a perspective view of the vascular stent.
Figure 3:
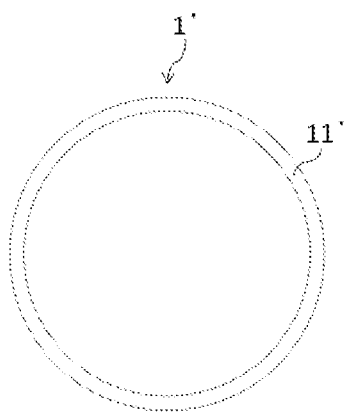
FIG. 3 is a cross-section of support rods of the vascular stent of FIG. 2.
Figure 4:
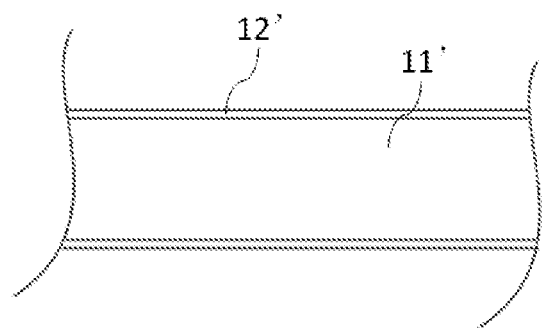
FIG. 4 is a partially enlarged schematic view of the drug coating on the support rod of the vascular stent of FIG. 2.

As shown in FIG. 2, the degradable vascular stent 1' is a tubular structure, which is formed by cutting the extruded tube from the polylactic acid based polymer. As shown in FIG. 3, the degradable vascular stent 1' comprises support rods 11' each of a certain thickness. As shown in FIG. 4, a drug coating 12' may be disposed on the support rod 11'.

Figure 5:
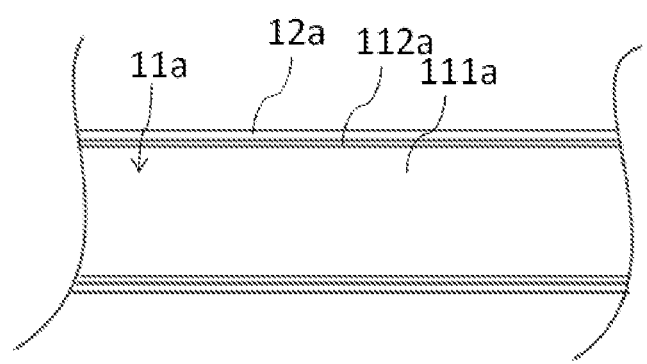
FIG. 5 is a partially enlarged schematic view of the wall of the degradable vascular stent capable of avoiding late restenosis according to one preferred embodiment of the present invention, showing the coating storage region.

FIG. 5 is a partially enlarged schematic view of the wall of the degradable vascular stent capable of avoiding late restenosis according to one preferred embodiment of the present invention. The wall comprises support rods 11a and a drug coating 12a coated on support rods 11a. The support rods 11a comprise a base region 111a at the center and a coating storage region 112a coated on the base region 111a. The drug coating 12a is coated on the coating storage region 112a.

Figure 6:
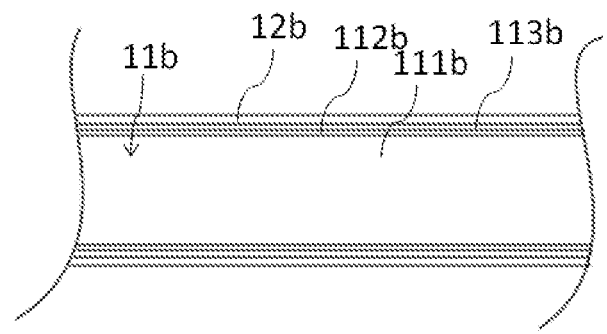
FIG. 6 is a partially enlarged schematic view of the wall of the degradable vascular stent capable of avoiding late restenosis according to another preferred embodiment of the present invention, showing the coating storage region with the isolation region.

FIG. 6 is a partially enlarged schematic view of the wall of the degradable vascular stent capable of avoiding late restenosis according to another preferred embodiment of the present invention. The wall also comprises support rods 11b and a drug coating 12b coated on support rods 11b. The support rods 11b comprise a base region 111b at the center, a coating storage region 112b coated on the base region 111b and a coating isolation region 113b coated on the coating storage region 112b. The drug coating 12b is coated on the coating isolation region 113b.

Figure 7:
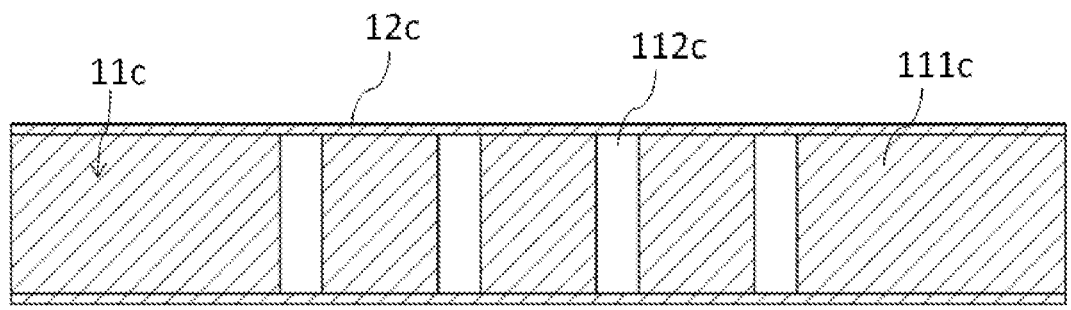
FIG. 7 is a partially enlarged schematic view of the wall of the degradable vascular stent capable of avoiding late restenosis according to yet another preferred embodiment of the present invention, showing the embedded storage region of through holes.

FIG. 7 is a partially enlarged schematic view of the wall of the degradable vascular stent capable of avoiding late restenosis according to yet another preferred embodiment of the present invention. The wall also comprises support rods 11c and a drug coating 12c coated on support rods 11c. The support rods 11c comprise a base region 111c and an embedded storage region 112c dispersed in the base region 111c formed by through holes extending through support rods 11c. The drug coating 12c is coated on the base region 111c and embedded storage region 112c.

Figure 8:
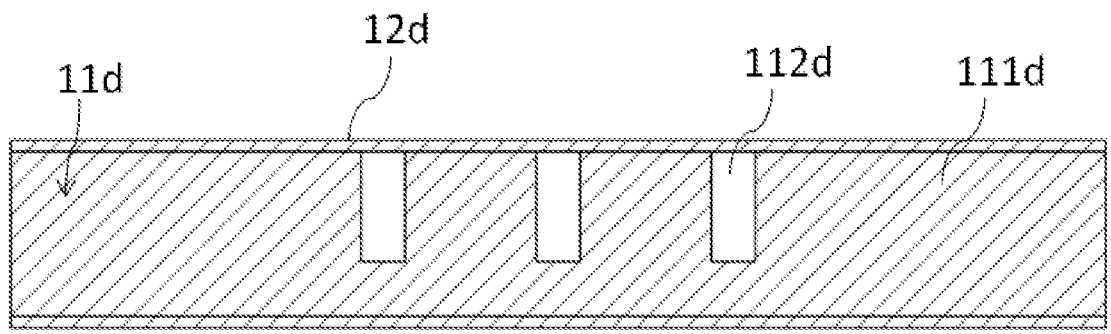
FIG. 8 is a partially enlarged schematic view of the wall of the degradable vascular stent capable of avoiding late restenosis according to yet another preferred embodiment of the present invention, showing the embedded storage region of blind holes.

FIG. 8 is a partially enlarged schematic view of the wall of the degradable vascular stent capable of avoiding late restenosis according to yet another preferred embodiment of the present invention. The wall also comprises support rods 11d and a drug coating 12d coated on support rods 11d. The support rods 11d comprise a base region 111d and an embedded storage region 112d dispersed in the base region 111d formed by blind holes concaving into support rods 11d from one side. The drug coating 12d is coated on the base region 111d and embedded storage region 112d.

Figure 9:
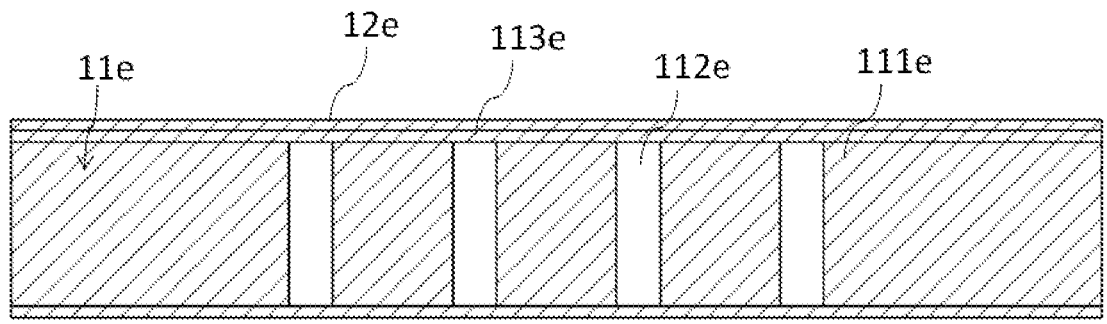
FIG. 9 is a partially enlarged schematic view of the wall of the degradable vascular stent capable of avoiding late restenosis according to yet another preferred embodiment of the present invention, showing the embedded storage region of through holes with the isolation region.

FIG. 9 is a partially enlarged schematic view of the wall of the degradable vascular stent capable of avoiding late restenosis according to yet another preferred embodiment of the present invention. The wall also comprises support rods 11e and a drug coating 12e coated on support rods 11e. The support rods 11e comprise a base region 111e and an embedded storage region 112e dispersed in the base region 111e formed by through holes extending through support rods 11e. The support rods 11e also comprises a coating isolation region 113e coated on the base region 111e and embedded storage region 112e. The drug coating 12e is coated on the coating isolation region 113e.

Figure 10:
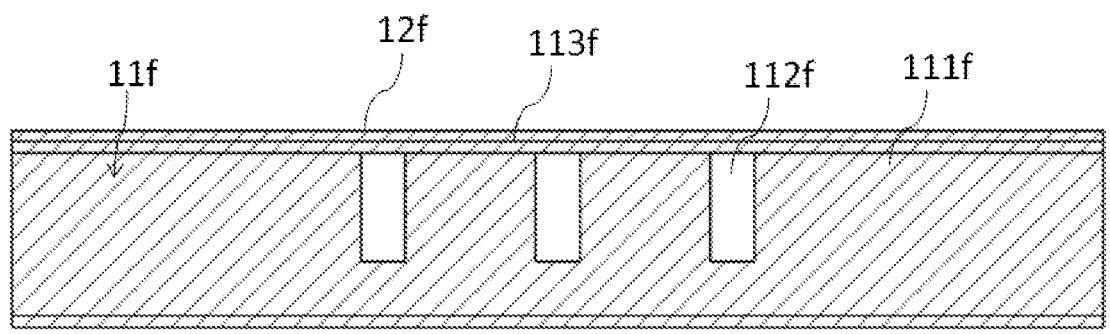
FIG. 10 is a partially enlarged schematic view of the wall of the degradable vascular stent capable of avoiding late restenosis according to yet another preferred embodiment of the present invention, showing the embedded storage region of blind holes with the isolation region.

FIG. 10 is a partially enlarged schematic view of the wall of the degradable vascular stent capable of avoiding late restenosis according to yet another preferred embodiment of the present invention. The wall also comprises support rods 11f and a drug coating 12f coated on support rods 11f. The support rods 11f comprise a base region 111f and an embedded storage region 112f dispersed in the base region 111f formed by blind holes concaving into support rods 11f from one side. The support rods 11f also comprises a coating isolation region 113f coated on the base region 111f and embedded storage region 112f. The drug coating 12f is coated on the coating isolation region 113f.

Figure 11:
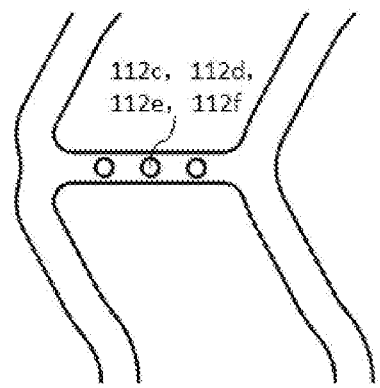
FIG. 11 is a schematic diagram of a first arrangement of the embedded storage region of through holes or blind holes.
Figure 12:
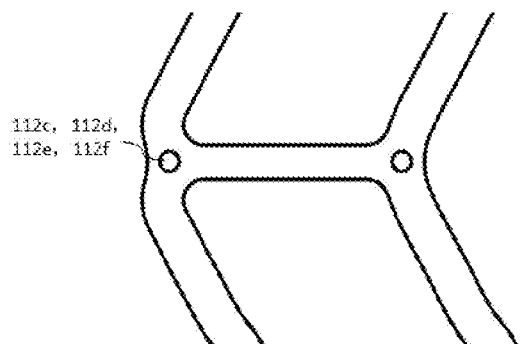
FIG. 12 is a schematic diagram of a second arrangement of the embedded storage region of through holes or blind holes.
Figure 13:
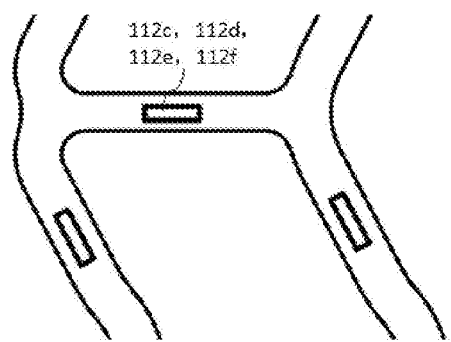
FIG. 13 is a schematic diagram of a third arrangement of the embedded storage region of through holes or blind holes.
Figure 14:
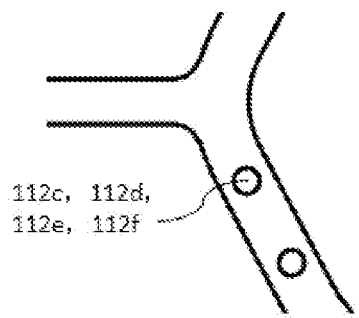
FIG. 14 is a schematic diagram of a fourth arrangement of the embedded storage region of through holes or blind holes.

FIGS. 11-14 show arrangements for the embedded storage regions 112c, 112d, 112e, 112f. As shown in FIG. 11, the embedded storage regions 112c, 112d, 112e, 112f may be provided by three circular through holes or blind holes in the middle of the support rod. As shown in FIG. 12, the embedded storage regions 112c, 112d, 112e, 112f may be provided by two circular through holes or blind holes each at the connection of two support rods. As shown in FIG. 13, the embedded storage regions 112c, 112d, 112e, 112f may be provided by three rectangular through holes or blind holes each in the middle of the support rod. As shown in FIG. 14, the embedded storage regions 112c, 112d, 112e, 112f may be provided by two circular through holes or blind holes each at an end of one support rod.

Figure 15:
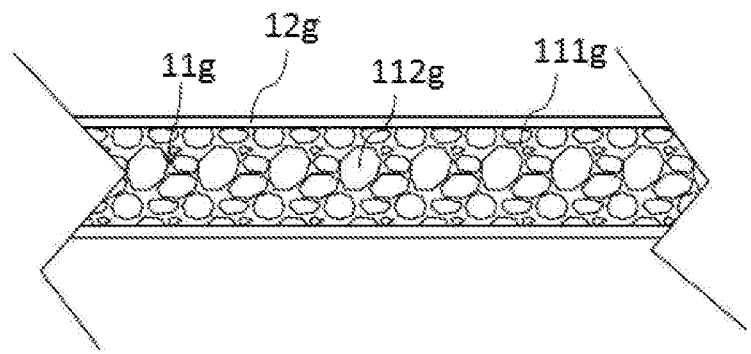
FIG. 15 is a partially enlarged schematic view of the wall of the degradable vascular stent capable of avoiding late restenosis according to yet another preferred embodiment of the present invention, showing the storage region dispersed in the base region.

FIG. 15 is a partially enlarged schematic view of the wall of the degradable vascular stent capable of avoiding late restenosis according to yet another preferred embodiment of the present invention. The wall also comprises support rods 11*g* and a drug coating 12*g* coated on support rods 11*g*. The support rods 11*g* comprise a base region 111*g* and a discrete storage region 112*g* dispersed in the base region 111*g* to form an integral part. The drug coating 12*g* is coated on the integral part.

Figure 16:
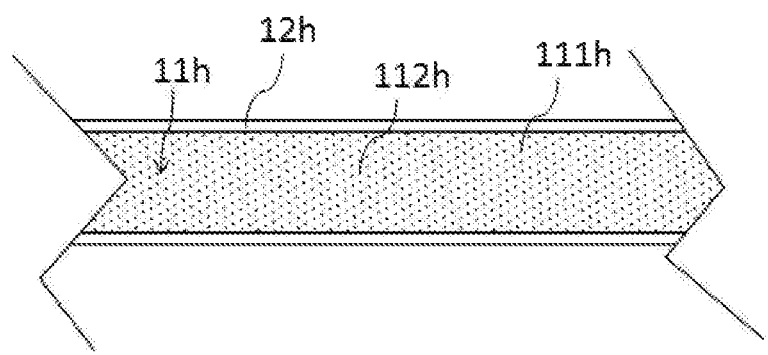
FIG. 16 is a partially enlarged schematic view of the wall of the degradable vascular stent capable of avoiding late restenosis according to yet another preferred embodiment of the present invention, showing the storage region distributed in the base region.

FIG. 16 is a partially enlarged schematic view of the wall of the degradable vascular stent capable of avoiding late restenosis according to yet another preferred embodiment of the present invention. The wall also comprises support rods 11*h* and a drug coating 12*h* coated on support rods 11*g*. The support rods 11*h* comprise a base region 111*h* and a storage region 112*h* evenly distributed in the base region 111*h* to form an integral part. The drug coating 12*h* is coated on the integral part.

Figure 17:
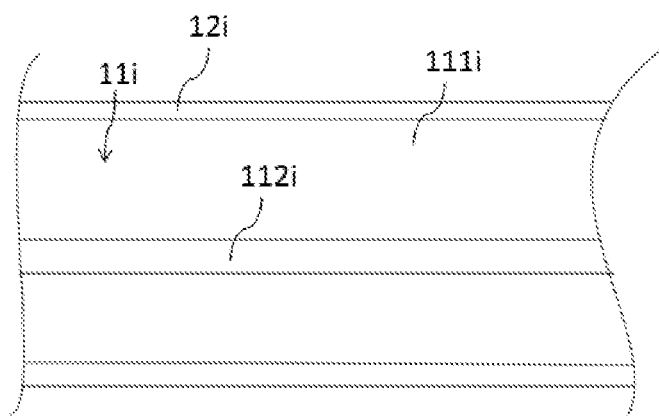
FIG. 17 is a partially enlarged schematic view of the wall of the degradable vascular stent capable of avoiding late restenosis according to yet another preferred embodiment of the present invention, showing the storage region disposed in the middle of the base region.

FIG. 17 is a partially enlarged schematic view of the wall of the degradable vascular stent capable of avoiding late restenosis according to yet another preferred embodiment of the present invention. The wall also comprises support rods 11*i* and a drug coating 12*i* coated on support rods 11*g*. The support rods 11*i* comprise a storage region 112*i* at the center and a base region 111*i* coated on the storage region 112*i*. The drug coating 12*i* is coated on the base region 111*i*.

In the present invention, the storage region 112 (including 112*a*, 112*b*, 112*c*, 112*d*, 112*e*, 112*f*, 112*g*, 112*h*, 112*i*, both here and below) is used for storing the active agent. Before the mass of the polylactic acid based polymer of the base region 111 (including 111*a*, 111*b*, 111*c*, 111*d*, 111*e*, 111*f*, 111*g*, 111*h*, 111*i*, both here and below) is decreased by 10-20%, the active agent in the storage region 112 is retained in structural units of the polylactic acid based polymer. After the mass of the polylactic acid based polymer of the base region 111 is decreased by 10-20%, the active agent in the storage region 112 is released from the storage region 112, until the polylactic acid based polymer is completely degraded.

In order to avoid the release of the active agent from the storage region 112 in an early stage after implantation (e.g., before the completion of vascular revascularization), the storage region 112 is completely covered by the drug coating 12. The active agent in the storage region 112 will not be released until the drug coating 12 is degraded and released.

The storage regions 112*a*, 112*b* are storage regions in the form of coating, which are wrapped inside the drug coatings 12*a*, 12*b*. If the active agent in the storage region 112*a* and 112*b* is an effective drug, the drug-polymer ratio in the coating can be less than ⅓. Thus, the release of the drug can be very slow, which can be as long as 2-3 years. If the active agent in the storage region 112*a*, 112*b* is an alkaline salt, the coating is usually a polymer coating of the alkaline salt. Further, in order to avoid the early release of the active agent from the storage region 112*b*, an isolation region 113*b* is disposed between the drug coating 12*b* and the storage region 112*b*. The degradation rate of the isolation region 113*b* is equivalent to the base region 111*b*. After the degradation of isolation region 113*b* is completed, the storage region 112*b* can be released.

The storage regions 112*c*, 112*d*, 112*e*, 112*f* are storage regions in the form of embedding, which are also wrapped inside the drug coatings 12*c*, 12*d*, 12*e*, 12*f*, while being embedded in the base regions 111*c*, 111*d*, 111*e*, 112*f*. Specifically, small pits are dispersed on the support rods, all of which provide the storage region. These small pits are opened on outer surfaces of the base region 111*c*, 111*d*, 111*e*, 112*f*. The small pits may penetrate through the base region 111*c*, 111*d*, 111*e*, 112*f* to form through holes, or may not penetrate through the base region 111*c*, 111*d*, 111*e*, 112*f* to form blind holes. In general, the small pits are preferably evenly dispersed in support rods where no stress is concentrated during deformation, so as to fully guarantee the physical performance of the stent even when it is compressed or expanded.

The small pits can be in any shape, such as a groove or a cylindrical hole. The elastic degradable polymer and active agent can be made into co-extruded fiber segments or capsules, which are squeezed into the small pits by tools in an interference fit. The active agent can also be directly inserted into the small pits. If an elastic polymer is used, the mass ratio of the active agent to the polymer can be more than 50%. The elastic degradable polymer can be 70/30 lactic acid and ε-caprolactone copolymer or any ratio of lactic acid and ε-caprolactone copolymer. Such polymer has elasticity and low melting point, and can be co-extruded with most active agents. Further, the small pits can be micro-blind holes, evenly dispersed on the outer surface of the base region. The size of the micro-blind holes is small enough not to affect the mechanical property of the stent. Preferably, the diameter of the micro-blind hole is between 100 nm and 5 μm. Optional active agent or a mixture of active agent and polymer may be provided in the storage region. The active agent can be injected into the micro-blind holes by pouring, dipping, brushing, spraying, etc. to form the storage region. A soluble polymer may be added when the tube is extruded. A solvent or solution can be used to dissolve out the soluble polymer to completely separate the polymer from the base region of the stent to form the micro-blind hole without damaging the material of base region. The size and number of micro-blind holes are adjusted by the ratio of the polymer and the time of dissolution. The more soluble polymers, the size of the micro-blind holes is larger. The longer the dissolution time, the number of micro-blind holes is bigger and the depth is greater.

The storage region 112*c*, 112*d*, 112*e*, 112*f* in the form of embedding is evenly or unevenly dispersed in the base region 111*c*, 111*d*, 111*e*, 111*f*. After the mass of the polymer of the base region 111*c*, 111*d*, 111*e*, 111*f* is decreased by 10-20%, the active agent in the storage region 112*c*, 112*d*, 112*e*, 112*f* can be released.

The storage region 112*g*, 112*h* is formed integrally with the base region 111*g*, 111*h*. They are fused and mixed into each other to form an integral part. The active agent is uniformly mixed in the melt or solution of the base region 111*g*, 111*h* to form a mixture, which is then extruded to form the tube, namely the active agent and the base region is co-extruded to form the tube. After extrusion, the active agent is evenly distributed in the base region, and the storage region and the base region form an integral part. Furthermore, the active agent can be made into nano-sized particles, and then co-extruded with the base region to form an integral structure of the storage region and the base region. The nano-scaled active agent can also improve the impact strength, tensile strength, modulus, thermal deformation temperature and other properties of the stent. In this way, a degradable polymer stent with a thinner wall thickness and a higher supporting force can be manufactured. Preferably, the particle size of the nano-scale active agent particles is between 1-100 nm.

The storage region 112*i* is a layered storage region, which is a completely separate region from the base region 111*i*. The storage region 112*i* is a mixture of an active agent and a degradable polymer. Such tube can be extruded with a twin-screw extruder, wherein the active agent is co-extruded with the degradable polymer by one screw to form the storage region. Such tube can also be formed by three coating layers, wherein the intermediate coating is the active agent layer. There are an intermediate storage region, a first outer base region and a second inner base region.

The available active agent in the storage region 112 may be a drug, which includes, but is not limited to, an anti-thrombotic drug, such as Heparin, Hirudin, Prostacyclin, Abciximab, etc.; an analgesic and anti-inflammatory drug, such as Mometasone Furoate, Dexamethasone (DXM), Methylprednisolone, Hydrocortisone, Cortisone Acetate, Prednisolone, Prednisone, Betamethasone, Triamcinolone, Triamcinolone, Beclomethasone, Fluticasone, Clobetasol, Clobetasone Butyrate, Halcinonide, Mometasone, Fluocinolone, Fluoromethalone, Deflazacort, Cloprednol, Vaderm, Bisphosphonate Liposomes, Aspirin, Phenylbutazone, Celecoxib, Rofecoxib, Parecoxib, Phenacetin, Indomethacin, Sulindac, Meloxicam, Ibuprofen, Diclofenac, etc.; an anti-vascular smooth muscle cells (VSMC) proliferation drug, such as Rapamycin (RAPM), Paclitaxel (PTX), Angiopeptin, Mycophenolic Acid, Tracolimus, Everolimus, Cyclosporine A, Methyl-RAPM, etc.; an anti-vascular smooth muscle cells (VSMC) migration drug, such as Batimastat, etc.; an endothelialization promoting drug, such as 17β-estradiol, vascular endothelial growth factor, etc.

The available active agent in the storage region 112 may be an inorganic antibacterial agent, which includes, but is not limited to, nano silver (particle size 10-100 nm), micron silver (particle size 2-100 μm), Ag ions, nano zinc (particle size 10-100 nm), zinc ion, micron zinc (particle size 2-100 μm), nano copper (particle size 10-100 nm), micron copper (particle size 2-100 μm), copper ion.

The available active agent in the storage region 112 may be a metal oxide, which includes a basic metal oxide, such as CaO, MgO, $Fe_2O_3$, FeO, etc.; and also includes amphoteric metal oxide, such as $Al_2O_3$, ZnO, BeO, etc.

The available active agent in the storage region 112 may be a degradable polymer with alkaline monomers, which includes, but is not limited to, chitosan and sodium alginate. The polymer including sodium alginate releases alkaline monomers after degradation. The alkaline monomers neutralize with the lactic acid monomers released by the degradation of polylactic acid, in order to reduce the acidity caused by the accumulation of lactic acid, thereby alleviating or avoiding the late inflammation. The alkaline polymer may also adjust the rate of degradation.

The available active agent in the storage region 112 may be an alkaline salt, which includes, but is not limited to, sodium carbonate ($Na_2CO_3$), sodium bicarbonate ($NaHCO_3$), potassium carbonate ($K_2CO_3$), calcium carbonate ($CaCO_3$), sodium sulfite ($Na_2SO_3$), sodium acetate ($CH_3COONa$), sodium sulfide ($Na_2S$), ferrous sulfide (FeS), sodium silicate ($Na_2SiO_3$), sodium phosphate ($Na_3PO_4$), sodium metaaluminate ($NaAlO_2$), sodium hypochlorite (NaClO), calcium hypochlorite ($Ca(ClO)_2$), ammonium bicarbonate ($NH_4HCO_3$), copper hydroxoliodate ($Cu(OH)IO_3$), antimony dioxide sulphate ($(SbO)_2SO_4$), malachite ($Cu_2(OH)_2CO_3$), hydroxyapatite ($Ca_5(PO_4)_3.(OH)$), cupric subcarbonate ($Cu_2(OH)_2CO_3$), and basic magnesium chloride (Mg(OH)Cl), etc.

Although the best mode and preferred embodiments of the present invention contemplated by the inventors have been described, these are not intended to limit the scope of the present invention. Many different changes or modifications of the features of the present invention could be made without departing from the spirit and scope of the underlying inventive concept. Therefore, any simple, equivalent changes and modifications made in accordance with the claims of the present invention and the contents of the description shall fall within the scope of the present invention. What is not described in detail in the present invention is conventional technical means.

Moreover, the individual components need not be formed in the disclosed shapes, or assembled in the disclosed configuration, but could be provided in virtually any shape and assembled in virtually any configuration. Furthermore, all the disclosed features of each disclosed embodiment can be combined with, or substituted for, the disclosed features of every other disclosed embodiment except where such features are mutually exclusive.

It is intended that the appended claims cover all such additions, modifications, and rearrangements. Expedient embodiments of the present invention are differentiated by the appended claims.

What is claimed is:

1. A degradable vascular stent capable of avoiding late restenosis, comprising:
   a base region formed by a polylactic acid based polymer;
   at least one storage region in which an active agent is stored; and
   an outer layer of a drug sustained release coating covered on the base region and/or the storage region;
   wherein before the mass of the polylactic acid based polymer of the base region is decreased by 10-20%, the active agent in the storage region is retained in structural units of the polylactic acid based polymer;
   wherein after the mass of the polylactic acid based polymer of the base region is decreased by 10-20%, the active agent in the storage region is released from the storage region;
   wherein the storage region is formed of an alkaline degradable polymer or a mixture of a polylactic acid based polymer and an alkaline degradable polymer; and
   wherein after the mass of the polymer of the base region is decreased by 10-20%, the alkaline degradable polymer is hydrolyzed to release alkaline monomers.

2. The degradable vascular stent according to claim 1, wherein the alkaline degradable polymer is chitosan or sodium alginate.

3. The degradable vascular stent according to claim 1, wherein the degradable vascular stent also comprises a coating isolation region covered by the outer layer.

4. The degradable vascular stent according to claim 1, wherein the storage region is a coating storage region on the base region, an embedded storage region in the base region, an integrated storage region formed integrally with the base region, or a layered storage region inside the base region.

5. The degradable vascular stent according to claim 4, wherein the embedded storage region is evenly distributed where no stress is concentrated during deformation.

6. A degradable vascular stent capable of avoiding late restenosis, comprising:
   a base region formed by a polylactic acid based polymer;
   at least one storage region in which an active agent is stored; and
   an outer layer of a drug sustained release coating covered on the base region and/or the storage region;
   wherein before the mass of the polylactic acid based polymer of the base region is decreased by 10-20%, the active agent in the storage region is retained in structural units of the polylactic acid based polymer;
   wherein after the mass of the polylactic acid based polymer of the base region is decreased by 10-20%, the active agent in the storage region is released from the storage region;

wherein the storage region is formed of a mixture of an alkaline salt dispersed in a polylactic acid based polymer; and wherein after the mass of the polymer of the base region is decreased by 10-20%, the alkaline salt is hydrolyzed to release alkaline monomers.

7. The degradable vascular stent according to claim 6, wherein the alkaline salt is selected from the group consisting of sodium carbonate, sodium bicarbonate, potassium carbonate, calcium carbonate, sodium sulfite, sodium acetate, sodium sulfide, ferrous sulfide, sodium silicate, sodium phosphate, sodium metaaluminate, sodium hypochlorite, calcium hypochlorite, ammonium bicarbonate, copper hydroxoliodate, antimony dioxide sulphate, malachite, hydroxyapatite, cupric subcarbonate, or basic magnesium chloride.

8. The degradable vascular stent according to claim 6, wherein the degradable vascular stent also comprises a coating isolation region covered by the outer layer.

9. The degradable vascular stent according to claim 6, wherein the storage region is a coating storage region on the base region, an embedded storage region in the base region, an integrated storage region formed integrally with the base region, or a layered storage region inside the base region.

10. The degradable vascular stent according to claim 9, wherein the embedded storage region is evenly distributed where no stress is concentrated during deformation.

\* \* \* \* \*